United States Patent [19]

Graham et al.

[11] Patent Number: 4,882,166

[45] Date of Patent: Nov. 21, 1989

[54] COMPOSITIONS COMPRISING ENCAPSULATED PARTICLES AND THEIR PREPARATION

[75] Inventors: Neil B. Graham, Bearsden; Abdul Rashid; Koritala P. Rao, both of Glasgow, all of Scotland

[73] Assignee: National Research Development Corporation, London, United Kingdom

[21] Appl. No.: 88,539

[22] Filed: Aug. 20, 1987

Related U.S. Application Data

[63] Continuation of Ser. No. 840,540, Mar. 17, 1986, abandoned, which is a continuation of Ser. No. 430,360, Sep. 30, 1982, abandoned.

[30] Foreign Application Priority Data

Sep. 30, 1981 [GB] United Kingdom ............... 8129575
Sep. 16, 1982 [GB] United Kingdom ............... 8226355

[51] Int. Cl.$^4$ ............................ A61K 9/58; B01J 13/02
[52] U.S. Cl. .............................. 424/462; 71/DIG. 1; 264/4.7; 424/45; 424/497; 427/213.3; 428/402.22; 428/402.24; 514/182; 514/814; 514/963; 524/847
[58] Field of Search ............... 264/4.7; 427/213.3; 428/402.22, 402.24; 424/462, 497; 514/963; 524/847

[56] References Cited

U.S. PATENT DOCUMENTS

| | | | |
|---|---|---|---|
| 2,969,330 | 1/1961 | Brynko | 264/4.7 X |
| 3,138,478 | 6/1964 | Hedman et al. | 427/212 |
| 3,318,846 | 5/1967 | Smith et al. | 526/330 |
| 3,390,050 | 6/1968 | Speiser | 424/497 |
| 3,544,500 | 12/1970 | Osmond et al. | 428/402.24 X |
| 3,577,516 | 5/1971 | Gould et al. | 424/443 X |
| 3,712,867 | 1/1973 | Schon et al. | 427/213.33 X |
| 3,714,102 | 1/1973 | Reiss | 428/402.24 X |
| 3,928,230 | 12/1975 | Unsworth et al. | 264/4.7 X |
| 4,269,821 | 5/1981 | Kreuter et al. | 424/489 |
| 4,438,258 | 3/1984 | Graham | 528/361 |
| 4,542,176 | 9/1985 | Graham | 524/548 X |
| 4,584,188 | 4/1986 | Graham | 424/419 |

FOREIGN PATENT DOCUMENTS

| | | |
|---|---|---|
| 0000291 | 1/1979 | European Pat. Off. |
| 1467843 | 12/1968 | Fed. Rep. of Germany |
| 2336936 | 7/1977 | France |
| 2017113 | 10/1979 | United Kingdom |
| 1572598 | 7/1980 | United Kingdom |

OTHER PUBLICATIONS

F. A. Carey et al.: *Advanced Organic Chemistry, Part B: Reactions and Synthesis*, Plenum Press, New York (1977) pp. 460–467.
*The Condensed Chemical Dictionary*, Tenth Edition; Revised by G. G. Hawley, VanNostrand Reinhold Co., New York (1981) p. 852.
Kirk–Othmer: *Encyclopedia of Chemical Technology*, Third Edition, vol. 22, p. 332, John Wiley & Sons, New York, 1983.

*Primary Examiner*—Richard D. Lovering
*Attorney, Agent, or Firm*—Oblon, Spivak, McClelland, Maier & Neustadt

[57] ABSTRACT

A composition which comprises at least one solid or liquid particle comprising at least one active substance, the or a plurality of such particles being encapsulated by the in situ cationic (co)polymerization there on of at least on cationically polymerizable monomer or prepolymer.

40 Claims, 5 Drawing Sheets

COMPOSITIONS COMPRISING ENCAPSULATED PARTICLES AND THEIR PREPARATION

This invention relates to compositions which comprise encapsulated particles; and to processes for their production. More particularly, but not exclusively, this invention relates to controlled release compositions which can provide sustained uniform rates of release of active substances; and to controlled release compositions which can provide pulsatile rates of release of active substances over at least a part of a period of sustained release, both release profiles being highly advantageous especially in numerous pharmaceutical applications.

By "pulsatile rates of release of active substance" is meant herein that the rate of release of the active substance has at least one maximum. Preferably, the rate of release has more than one maximum. It is further preferred that the or each maximum is of sufficient sharpness and magnitude and of appropriate incidence to procure the desired effect.

However, this invention also relates to compositions which, instead of providing release of active substance, either protect it, or alter its surface properties, by the encapsulation.

According, therefore, to one aspect of this invention, there is provided a composition which comprises at least one solid or liquid particle comprising at least one active substance (and, preferably, one which comprises a plurality of such solid or liquid particles), the or a plurality of such particles being encapsulated by the in situ cationic (co)polymerisation thereon of at least one cationically polymerisable monomer or prepolymer.

In accordance with a further aspect of this invention, there is provided a process for the preparation of a composition which comprises at least one solid or liquid particle comprising at least one active substance, the or a plurality of such particles being encapsulated by a (co)polymer, which process comprises treating the or a plurality of such articles by absorbing thereon at least one amphipathic compound; if necessary, activating the amphipathic compound with a Bronsted or a Lewis acid so that it can function as an initiator as a comonomer in cationic polymerisation; and encapsulating the or a plurality of the treated particles by the in situ (co)-polymerisation thereon of at least one cationically polymerisable monomer or prepolymer.

By "(co)polymer" and "(co)polymerisation" are meant herein, respectively, homopolymer or copolymer and homopolymerisation or copolymerisation.

Where, as is preferred, the composition of the invention comprises a plurality of solid or liquid particles it is found, especially at smaller average particle sizes, that either some particles escape encapsulation in toto or, because of aggregation, a plurality of particles are incorporated within the same encapsulating (co)polymeric layer. It is, however, found that these defects account for a very small proportion of the treated particles.

Compositions of this invention also include admixtures of encapsulated particles as herein defined with unencapsulated particles or with particles which have been encapsulated in a different manner.

Classes of cationically polymerisable monomer or prepolymer useful in preparing compositions of this invention include:

(a) a substituted or unsubstituted, cyclic or linear, mono- or poly-vinyl (thio)ether;

(b) a compound, other than as defined in (a), comprising at least one substituted or unsubstituted 3- or 4-membered ring comprising an oxa- or thia-hetero atom;

(c) a substituted or unsubstituted cyclic aliphatic anhydride;

(d) a substituted or unsubstituted aliphatic aldehyde;

(e) a substituted or unsubstituted mono- or poly-vinyl aromatic hydrocarbon; or (f) a substituted or unsubstituted mono- or poly-isocyanate By "vinyl (thio)ether" is meant herein a compound comprising at least one $>C=C-O-$ or $>C=C-S-$ group.

It is preferred that the vinyl (thio)ether (a) is a cyclic vinyl (thio)ether and it is especially preferred that the or each oxygen (or sulphur) atom is a hetero atom and that the or each double bond conjugated therewith is contained in the hetero ring. Examples of linear vinyl (thio)ethers include substituted or unsubstituted alkyl, suitably $C_1$ to $C_5$ alkyl, vinyl (thio)ethers such as methyl vinyl ether and ethyl vinyl ether. Examples of cyclic vinyl (thio)ethers (which are of particular prominence in this invention) are discussed below.

Preferred compounds (b) include mono- and poly-epoxides and episulphides, for example an aromatic or aliphatic diepoxide, especially such as bisphenol A, its homologues and its cycloaliphatic analogues. Other such compounds include $\beta$-latones such as propiolactone.

Examples of compound (c) include substituted or unsubstituted maleic, succinic or glutaric anhydrides.

Class (e) is a preferred class of compound and includes styrene, $\alpha$-methyl styrene, vinyl toluene, indene and divinyl benzene, styrene or divinyl benzene being preferred.

Cationically polymerisable monomers or prepolymers as herein described may be in situ cationically polymerised on the or a plurality of the particles alone or a mixture of such monomers and/or prepolymers may be used; for example a mixture of such monomers and/or prepolymers with at least 50% by weight, preferably at least 70% by weight, of a cyclic vinyl (thio)ether. However, it has been found that styrene provides a controlled release composition exhibiting a particularly sustained rate of release on being in situ cationically polymerised to encapsulate a plurality of particles of a drug; for example pyrimethamine.

In accordance with a preferred feature of this invention, the composition of this invention is a controlled release composition. In accordance with a particularly preferred feature of this invention, especially where pulsatile rates of release of active substance are desired, the encapsulating (co)polymer is hydrolysable. Preferably, such a (co)polymer comprises at least one nonpendant hydrolysable carboxylic ester, carbonate ester, amide, urethane, ketal or phosphate function.

In accordance with a particularly preferred feature of this invention, the cationically polymerisable monomer or prepolymer comprises a cyclic (thio)ether of the formula:

in which:

$R_1$, $R_2$ and $R_4$, which may be the same or different, each represent a hydrogen atom or a substituted or unsubstituted hydrocarbyl or hydrocarbyloxy group;

$R_3$ represents a substituted or unsubstituted methylene, ethylene or 1,3-propylene group;

$R_5$ represents a monovalent polymerisable group;

Q represents an oxygen or a sulphur atom; and

X represents:

in which:

Y represents an oxygen atom or an —$NR_6$— group wherein $R_6$ represents any of the values which $R_1$ may assume;

a is 0 or 1;

b is 0 or 1;

c is 1 or 2;

d is 0 or 1; with the proviso that at least one of b or d is 1, or a prepolymer thereof.

X may, as shown, represent any hydrolysable carboxylic acid ester, carbonate ester or oxalate ester function, or an amide analogue. Preferably, however, X represents —COO— or —$CH_2OCO$—.

Particularly preferred polymerisable cyclic ethers have the formula:

in which:

$R_1$, $R_2$ and $R_4$, which may be the same or different, and $R_5$ are as herein defined.

$R_5$ may suitably represent any monomeric, oligomeric or polymeric group provided that it comprises a group which can participate in the in situ cationic (co)-polymerisation; for example, those derivable from monomers or prepolymers (a) to (f) mentioned hereinbefore. Preferred examples are vinyl (thio)ether and epoxy groups.

It is particularly preferred that $R_5$ represents a group derived from a cyclic vinyl (thio)ether, especially of the formula:

in which:

$R_1'$, $R_2'$, $R_3'$ and $R_4'$, which may be the same or different, represent any of the values which $R_1$, $R_2$, $R_3$ and $R_4$ may assume;

M represents the group —ZX'—;

Q' represents any oxygen or sulphur atom;

X' represents any of the values which X may assume; and

Z represents a single bond or a carbon-linked mono-, oligo- or homo- or co-poly (substituted or unsubstituted hydrocarbylene or hydrocarbyleneoxy residue) such as a substituted or unsubstituted arylene, alkylene or alkylene oxide group.

Especially preferred polymerisable cyclic ethers are the reaction products formed by subjecting one or a mixture of dihydropyran aldehydes to disproportionation by the Tischenko reaction; they have the formula:

in which:

$R_1$, $R_2$ and $R_4$, which may be same or different, are as herein defined; and

$R_1'$, $R_2'$, and $R_4'$, which may be the same or different, represent any of the values which $R_1$, $R_2$, and $R_4$ respectively may assume. A preferred such compound as acrolein tetramer (in which $R_1$ all represent hydrogen atoms).

Polymerisable cyclic ethers wherein X comprises a —COO— or —$CH_2OCO$— group may conveniently be prepared from the tetramer of the corresponding unsaturated aldehyde produced by the Tischenko reaction; namely:

Thus, cyclic ethers wherein X comprises a —COO— group may be prepared by reaction of the tetramer with an alcohol $R_5OH$ using a transesterification catalyst and reaction conditions:

Cyclic ethers wherein X comprises a —$CH_2OCO$— group may be prepared by reaction of the tetramer with a lower alkyl carboxylic acid ester $R_5COOR_9$ represents a lower alkyl group using a transesterification catalyst and reaction conditions:

The respective by-products may also be esterified with $R_5COOH_9$ or $R_5OH$ to give, correspondingly:

The corresponding amides may be prepared analogously.

Cyclic ethers where X comprises a —COO— group may also be obtained by mild oxidation of the dimer of the corresponding unsaturated aldehyde, followed by esterification of the salt for example the silver salt.

Meta-carbonates and oxalates may be obtained, respectively, by esterification:

(Chloroformic esters, such as ethyl chloroformate, may also be used.)

It is, however, to be stressed that acrolein tetramer is readily prepared from acrolein which is a commercially available material; can readily be purified; and has been found to be satisfactory in the practice of this invention.

The cationically polymerisable monomer or prepolymer may also comprise a cyclic (thio)ether of the formula:

in which:

$R_1$, $R_2$, $R_3$, $R_4$, $R_5$, and Q are as hereinabove defined; and X" represents:

in which:

Y represents an oxygen atom or an —$NR_6$— group wherein

$R_6$ represents any of the values which $R_1$ may assume;

a is 0 or 1;

b is 0 or 1;

c is 0 or 1; with the proviso that b+c is 1, or a prepolymer thereof.

The polymerisable cyclic (thio)ether may also comprise the aldol condensation product of at least one dimer of the corresponding unsaturated aldehyde:

namely:

or a prepolymer thereof.

The polymerisable cyclic (thio)ether (i) may further comprise the Diels-Alder product of reacting at least one unsaturated aldehyde with a polyvinyl ether or a polyhydroxy compound:

wherein:

$R_7$ represents an n-valent hydrocarbon or poly(oxyhydrocarbon) residue of an n-hydroxy compound, or a prepolymer thereof.

The polymerisable cyclic (thio)ether (i) may further comprise wherein:

$R_8$ represents an n-valent non-hydrolysable bridging residue, or a prepolymer thereof.

These last four depicted compounds give rise to compositions of the invention which are less readily hydrolysed. Their use gives a first method for providing a controlled release composition according to the invention with a desired rate of hydrolysis.

The degree of hydrolytic stability provided can also be accurately tailored by a number of other different mechanisms. Thus, homologues of acrolein tetramer, for example methacrolein tetramer or the mixed acrolein/methacrolein tetramer, exert steric hindrance, which increases as the size of $R_4$ increases, to the hydrolysable ester or amide function X and thereby increases the stability of the derivative. Mono-, di and poly-carboxy and phenolic hydroxy substituted hydrocarbons form derivatives which are prone to hydrolysis and which yield catalytic acidic species thereon; derivatives where X and X', which may be the same or different, each represent a —COO— or —CH$_2$OCO— group and Z represents a substituted or unsubstituted hydrocarbylene group also facilitate hydrolysis. Examples include:

Furthermore, derivatives which retain one or more carboxy or hydroxy groups comprise a relatively high level or water which itself facilitates hydrolysis.

The groups R$_1$, R$_2$ and R$_4$ may each represent a substituted or unsubstituted hydrocarbyl or hydrocarbyloxy group: examples include unsubstituted or halosubstituted C$_1$ to C$_4$ alkyl, such as methyl or ethyl; unsubstituted C$_6$ to C$_{10}$ aryl or aralkyl such as phenyl or benzyl; and oxy analogues. In the case of R$_4$, increase in the size of the group increases the steric hindrance to any hydrolysable ester or amide function and thereby increases the stability of the hydrogel. It is preferred, however, from the standpoint of ease of preparation and availability, that at least one, and preferably all, of R$_1$, R$_2$ and R$_4$ represents a hydrogen atom. The group R$_3$ may represent a mono- or poly-substituted ethylene group, preferably an unsubstituted ethylene group; that is, a dihydro(thio)pyran derivative.

Preferred such compounds (i) are esters; that is, those compounds of the above formula wherein Q represents an oxygen atom, especially dihydropyrans.

The process of the present invention requires that the or a plurality of the particles to be encapsulated should be treated by absorbing thereon at least one amphipathic compound. Where the compound is sufficiently acidic to initiate the cationic polymerisation it need not be activated; where this is not the case, however, it should be activated by a Bronsted or Lewis acid. A monofunctional such amphipathic compound can only act as an initiator for the cationic polymerisation but a difunctional such amphipathic compound can participate in the cationic polymerisation while an amphipathic compound with higher functionality can also effect cross-linking of the encapsulating copolyer. It is believed (though not ascertained), however, that the primary function of the amphipathic compound is to provide high surface concentrations of initiator for the in situ cationic polymerisation on the surface of the or a plurality of the particles to be encapsulated.

According to a preferred feature of the invention, there is provided a composition according to the invention wherein the or a plurality of such particles is encapsulated by in situ cationic copolymerisation and the cationically polymerisable comonomer or prepolymer comprises at least one amphipathic compound polyfunctionally reactible with at least one cationically polymerisable monomer or prepolymer as herein defined.

In accordance with a preferred feature of this invention the amphipathic compound is a C$_6$ to C$_{36}$ saturated or unsaturated, aliphatic, cycloaliphatic, aromatic or araliphatic hydrocarbon which is substituted by a plurality of functional groups which comprise one or more hydroxyl groups, mercaptan groups, carboxylic acid groups and/or amide groups; and/or ester and/or amide groups which are themselves substituted by one or more of the said functional groups. Preferably, the amphipathic compound (ii) is a monoester of a C$_{10}$ to C$_{20}$ monocarboxylic acid or a C$_{10}$ to C$_{20}$ monoalcohol with, correspondingly, a polyol or polycarboxylic acid, or with a hydroxy acid, for example, a monoglyceride such as $\alpha$-monopalmitin, $\alpha$-monolein, and $\alpha$-monostearin.

The encapsulating (co)polymer may be chemically cross-linked; good results are, however, obtained with linear (co)polymers.

The present invention is of broad applicability in the formulation of active substances releasable as aforesaid particularly, but not exclusively, biologically active substances. Examples of industries where the invention is applicable include the pharmaceutical, cosmetic, veterinary, agricultural, food, paint and stationery industries. Examples of classes of active substances which may be incorporated in the controlled release compositions of the present invention include pigments, such as titania, flavourings, pharmaceuticals, bacteriostats, viruscides, pesticides such as insecticides, nematicides, molluscicides and larvicides, herbicides, fungicides, algaecides, topical or dermatological agents, anti-foulants for marine growth prevention, proteins, for example enzymes, peptides, microbiological and plant hydroculture salts and nutrients and preservatives, veterinary trace metal formulations and other growth promoting factors used in animal husbandry; for example anti-anaemic preparations and anabolic steroids. Of particular interest are compositions of the present invention comprising, as biologically active substance, at least one pharmaceutical.

The compositions of this invention thus find wide application in medical and surgical, including veterinary, contexts and in horticulture and agriculture as well as outside these areas.

Specific classes of drug which may be utilised in a controlled release composition of the invention include abortifacients such as prostaglandins, hypnotics, sedatives, tranquilisers, anti-pyretics, anti-inflammatory agents, anti-histamines, anti-tussives, anti-convulsants, muscle relaxants, anti-tumor agents, for example those for the treatment of malignant neoplasia, local anaesthetics, anti-Parkinson agents, topical or dermatological agents, diuretics, for example those containing potassium, such as potassium iodide, preparations for the treatment of mental illness, for example preparations containing lithium for use in the treatment of manic depression or containing prostaglandins for the treatment of schizophrenia, anti-spasmodics, anti-ulcer agents, preparations containing various substances for the treatment of infection by pathogens including antifungal agents, for example metronidazole, anti-parasitic agents and other anti-microbials, anti-malarials, cardiovascular agents, preparations containing hormones, for example androgenic, oestrogenic and progestogenic hormones, notably steriods such as oestradiol, sympathomimethic agents, hypoglycaemic agents, contraceptives, nutritional agents, preparations containing enzymes of various types of activity, for example chymotrypsin, preparations containing analgesics, for example aspirin, and agents with many other types of action including nematocides and other agents of veterinary application. Mixtures of active substances may be incorporated into the controlled release composition.

It is a particularly preferred feature of the invention that the controlled release composition is a contraceptive composition suitably containing, as active substance, at least one natural or synthetic steroid sex hormone for example an oestrogen or progestogen. Suitably progestogens include the natural progesterone and its synthetic analogues, including 11-dehydroprogesterone, dihydroxyprogesterone acetophenide, delalutin, 21-fluor-17-acetoxy-6 α-methylprogesterone, medroxyprogesterone acetate, megestrol acetate, chlormadinone acetate, ethisterone, dimethisterone, A-norprogesterone, 19-norprogesteone, 21-norprogesterone, normethandrone, norethynodrel, northindrone and its acetate, DL- and D-norgestrel, norgestrenone, ethynodiol diacetate, lynstrenol, ethynylestradiol, retroprogesterone, dydrogesterone, norvinodrel, quingestranol acetate, norethisterone and its acetate and oenanthate, anagestrone acetate, medrogestone, clomagestone, allyl estrenol and cingestol, preferably progesterone. Suitable oestrogens include the natural β-oestradiol and its synthetic analogues, principally ethinyloestradiol or mestranol, preferably β-oestradiol or its oenanthate.

The controlled release compositions of this invention are also useful in the treatment of diabetes and pernicious anaemia where, for example, the sustained release of insulin and cobalamin, respectively, may be utilised. They are also particularly suited to treatment, both propylactic and therapeutic, of tropical diseases; for example malaria, leprosy, schistosomiasis and clonorchiasis. Examples of drugs which can be used as biologically active substance in sustained release compositions of this invention for the treatment of these and other tropical diseases include quinine, sulphonamides, rifampcin, clofazimine, thiambutosine, chlorphenyl derivatives, chlorguamide, cycloguanil, pyrimethamine, sulphadiazine, trimethoprim, quinoline derivatives such as pamaquine, chloroquine, pentaquine, primaquine and amodiquine, pararosaniline, sulphamethizole, quinacrine, dapsone, sodium sulphoxone, sulphetrone, sodium hydnocarpate and sodium chaulmoograte. Drugs of particular effectiveness are cycloguanil, pyrimethamine and sulphadiazine.

Antibiotics, such as tetracycline (both as free base and hydrochloride or a mixture thereof) have also been found to be efficacious in the treatment of tropical disease in compositions according to this invention.

The controlled release compositions of this invention are also very well suited to veterinary applications. Examples include liquid depot preparations of antibiotics for general antibacterial activity and also in the treatment of anaplasmosis in cattle; preparations for provision of a wide spectrum of activity against both ectoparasites, for example mites, and endoparasites including arthropods, arrested larvae stages of nematodes, lungworms and general strongyles: these may comprise avermectins; preparations for provision of activity against trematode, cestode and roundworm infections; these may comprise amoscanate and praziquantel; preparations for provision of activity against theileria in cattle: these may comprise biologically active naphthoquinones such as menoctone; preparations for provision of activity against babesiosis in cattle, horses and dogs: these may comprise berenil, amidocarb and diampron; preparations for provision of activity against liver fluke in sheep and cattle and against Haemonchus species: these may comprise closantel.

Another important veterinary application of the controlled release composition of the invention is, with appropriate concentration of steroid hormone, to ensure that female livestock, such as cattle and sheep, are fertile when presented to an active male.

The active substance used in the preparation of a controlled release composition in accordance with this invention may be incorporated as a monolithic particle: it is preferred, however, that the controlled release composition comprises a plurality of finely-divided particles, suitably of average particle size not exceeding 2,000$\mu$, for example not exceeding 1,500$\mu$, preferably of average particle size from 5$\mu$ to 1,000$\mu$, for example 500$\mu$ or 100$\mu$, especially from 10$\mu$ to 50$\mu$. Such a controlled release composition may be formulated and preferably dispersed in a inert liquid diluent. Where the diluent is sterile the controlled release compositions of the invention may be used as an injectable dosage form, especially as an injectable contraceptive or in the treatment of tropical disease. Instead, the controlled release composition may be formulated and preferably dispersed in an inert vapour such as a polyhalogenated lower alkane which, under superatmospheric pressure, may be used as an aerosol dosage form.

The controlled release composition may also be tableted, optionally with an excipient; or incorporated, as encapsulated powder, within a hydrolysable container: for example a hard or soft gelatin capsule; or incorporated in a chewing gum base. These formulations are suitable as oral dosage forms.

In accordance with a further aspect of this invention, there is also provided a controlled release composition as herein described for use in therapeutic, for example the treatment of tropical disease or contraceptive methods of treatment of an animal or human patient.

This invention provides a method of therapeutic treatment of a human or animal patient, such as for contraception or the treatment of tropical disease, which comprises applying to the patient an effective dosage of a controlled release composition as herein described.

The compositions of the invention may also be used to protect or alter the surface of the active substance. For example, pigments can be encapsulated to modify their surface properties so as to render them easily— or (if of colloidal dimensions) auto-dispersible in, for example, a paint composition. The encapsulation can also protect the paint composition for photodegradation catalysed by the pigment.

As mentioned previously, it is preferred that the active substance comprises a plurality of particles, especially of average particle size not exceeding 1,000$\mu$. Suitably, the active substance is suspended in a liquid which is an inert non-solvent. In the case of steroid hormones and also inorganic pigments one or more aliphatic or aromatic liquid hydrocarbons is found to be suitable.

It is desirable that the amphipathic compound, which is preferably a $C_6$ to $C_{36}$ saturated or unsaturated, aliphatic, cycloaliphatic, aromatic or araliphatic hydrocarbon which is substituted by a plurality of functional groups which comprise one or more hydroxyl groups, mercaptan groups, carboxylic acid groups and/or amide groups; and/or ester and/or amide groups which are themselves substituted by one or more of the said functional groups, is dissolved in a solvent which is compatible with, and preferably identical to, the inert non-solvent for the active substance. Such a solvent should have a zero or positive, preferably positive, spreading coefficient. The amount of amphipathic compound should be commensurate with the amount calculated, from surface chemistry predeterminations of the BET surface area of the particles of active substance and of the average area of amphipathic molecules adsorbed on to the particular active substance, for a desired coating thickness together with about 5% to 20% by weight excess for dissolution. Particularly preferred amphipathic compounds are monoglycerides such as α-monopalmitin, α-monoolein, and α-monostearin.

Where the amphipathic compound is a free acid it is not normally necessary to activate it with a Bronsted or Lewis acid. In accordance with a preferred feature of the invention, however activation is preferred. Suitable Bronsted acids include strong mineral acids which are not redox reagents under the polymerisation conditions such as hydrochloric and sulphuric acid, perchloric acid and silicofluoric acid, tosylic acid, brosylic acid and the adduct or methanol and boron trifluoride. Suitable Lewis acids include boron trifluoride and its adduct with diethyl ether, boron trichloride, boron tribromide, aluminium trichloride, aluminium tribromide, gallium trichloride, germanium tetrachloride, tin tetrabromide, zinc chloride and ferric chloride, boron trifluoride etherate being preferred. Preferably the acid is dissolved in a solvent which is compatible with, and preferably identical to, the inert non-solvent for the active substance.

The or each comonomer is suitably a polymerisable cyclic (thio)ether as herein described, or is a prepolymer thereof with at least one polyhydric alcohol such as glycerol. Preparation of the prepolymers may be effected in accordance with out copending application GB 2090264A. Preferably the comonomer is dissolved in a solvent which is compatible, with and preferably identical to, the inert non-solvent for the active substance.

The in in situ cationic polymerisation may be effected at a temperature from −70° to 120° C., desirably from 50° to 100° C. preferably ambient temperature. Ambient or autogenous pressure may be used.

Lower temperatures may, in particular, be utilised where a substituted or unsubstituted acrolein tetramer or other monomers or mixture of monomers free from proton donating species is used as monomer or where a linear (co)polymer is to be formed. Polymerisation at low temperatures is particularly useful where the active substance is a liquid at ambient temperature and pressure. The liquid particles can be solidified and the process of this invention performed on them prior to returning to ambient temperature.

The process of the invention may also be repeated a plurality of times to provide a multi-encapsulated composition of the invention. Each encapsulating (co)polymeric layer may be the same or different, and may be a monolayer (as in the Examples).

The process of this invention is particularly useful in the preparation of stable liposome analogues with long shelf life.

The following Examples illustrate the invention. All glassware used in the experimentation was thoroughly cleaned with permanganic acid (potassium permanganate in concentrated sulphuric acid) followed by a plurality of copious rinses with tap water and thereafter with double distilled water. The thus cleaned glassware was then dried in a clean, electrically-heated oven at a temperature above 100° C. All liquid reaction media were redistilled prior to use.

EXAMPLE 1

1.0597 g of β-oestradiol (ex Sigma Chemical Co., 0–53μ particles of BET surface area 8.5 $m^2g^{-1}$), as active substance, were placed in a 50 $cm^3$ glass tube with a ground glass stopper and mechanically shaken for about 20 h at room temperature with 3.8 $cm^3$ of a solution of 0.2634 g of α-monoolein (ex Sigma Chemical Co. comprising about 10% β-isomer), as amphipathic compound, in 100 $cm^3$ of n-heptane (analytical reagent ex Fisons). The tube then contained active substance on to which the amphipathic compound had been adsorbed which was in equilibrium with its bulk concentration in the solution. The contents of the tube were next centrifuged and about half of the supernatant liquid was pipetted off.

A solution of boron trifluoride etherate (laboratory reagent ex BDH Ltd.) as activator, was prepared by mechanically shaking 1 $cm^3$ of the adduct with 10 $cm^3$ of n-heptane for about 2 h at room temperature. The suspension was allowed to settle and the supernatant used as activator solution. 1 $cm^3$ of the activator solution was then added to the glass tube containing the active substance on to which the amphipathic compound had been adsorbed and the mixture was mechanically shaken for about 0.75 h, centrifuged and the supernatant liquid was pipetted off.

The powder thus obtained was next mechanically shaken in the presence of 10 $cm^3$ of n-heptane for about 0.3 h at room temperature with 0.714 $cm^3$ of solution of 0.9688 g of acrolein tetramer (ex Canadian Industries Ltd., and redistilled three times under reduced pressure in a stream of dry nitrogen) in 100 $cm^3$ of n-heptane and filtered. The encapsulated material so formed was finally washed with n-heptane, dried and kept in a sample bottle.

For clarity, the calculation of the required amount of amphilpathic compound and acrolein tetramer is given below in extenso.

| | |
|---|---|
| Wt. of β-oestradiol crystals of predetermined BET surface area 8.5 $m^2g^{-1}$: | 1.0597 g |
| Total surface area: | $9.00745 \times 10^{20}$ $Å^2$ |
| Number molecules of amphipathic compound of predetermined area of adsorption on to the β-oestradiol crystals 53.25 $Å^2$ for monolayer coverage: | $\dfrac{9.00745 \times 10^{20}}{53.25}$ $= 1.69154 \times 10^{19}$ |
| Number moles amphipathic required for monolayer coverage: | $\dfrac{1.6915 \times 10^{19}}{2.80846 \times 10^{-5} \text{ mol.}}$ $= 3.8$ $cm^3$ of solution |
| Mol. equivalent of acrolein | |

| | |
|---|---|
| tetramer + 10% excess | = 3.0893 × 10⁻⁵ mol.<br>= 0.714 cm³ of solution |

EXAMPLE 2

Example 1 was repeated except that 10 cm³ of the acrolein tetramer solution were utilised. The encapsulated material so formed had a thicker coating.

EXAMPLE 3

Example 1 was repeated and the encapsulated material so formed was then used as active substance on which the process of the whole example was again performed to provide a second encapsulation, it being assumed that the surface area of the active substance remained substantially unaltered after the first encapsulation.

EXAMPLE 4

This example describes the use of a different, prepolymeric coating material. In the preparation of the prepolymer all the reactants, catalysts and solvent were thoroughly dried.

1.860 g of glycerol (analytical reagent ex Fisons dried at 95°–100° C. under reduced pressure in dry nitrogen) were added to 60 cm³ of methyl acetate (laboratory reagent ex Fisons refluxed for 24 h with calcium hydride), as solvent, in a round-bottomed flask fitted with a condenser, drying tube and dropping funnel containing a magnetic stirring bar and 13.44 g of acrolein tetramer dissolved in 40 cm³ of methyl acetate. The flask was heated and stirred with a mantle cum stirrer. Five minutes after reflux had commenced 0.153 g of p-toluenesulphonic acid (analytical reagent ex Fisons dried at 40° C. under reduced pressure for 20 h) was added to the flask and, 10 minutes thereafter, the acrolein tetramer solution was added dropwise. The reaction was found to be complete after 2 h (by periodic removal of samples through a self-seating septum and monitoring the disappearance of the —OH IR absorption near 3,500 cm⁻¹). The solution was then concentrated to about 95% solids using a rotary evaporator.

The concentrated prepolymer so formed (3:1 mole ratio of acrolein tetramer:glycerol) was next dissolved in 30 cm³ of a 40:60 v/v ratio mixture of n-heptane with toluene (analytical reagent ex Fisons), the mixture having a solubility parameter, δ, of 8.3. The prepolymer solution was then used in place of the acrolein tetramer solution of Example 1. The encapsulated material so formed was finally washed with the n-heptane/toluene mixture, dried at 40° C. under reduced pressure for 4 h and kept in a sample bottle.

EXAMPLE 5

1.056 g of titanium dioxide (rutile) ex Tioxide International supplied as uncoated and obtained from the chloride process with particles of BET surface area 7.9 m²g⁻¹) were tumbled for 20 h with 3.72 cm³ of the solution of α-monoolein in n-heptane. The remainder of the encapsulation process was then effected in the manner described in Example 1; in particular, the amount of the amphipathic compound solution was calculated as described in Example 1 but on the basis of its predetermined area per adsorbed molecule on to the TiO₂ crystals of 50.44 Å².

EXAMPLE 6

This Example describes electron microscopy effected on the encapsulated products of the preceding examples.

In each case, aluminium stubs cleaned with acetone (ex Koch Light Lab. Ltd., analar purity) for 24 h were spotted with the encapsulated material. The spotted stubs were the sputtered with gold and observed under a scanning electron microscope (Philips, model PSEM 500).

Encapsulated product from Example 1 exhibited a wide variety of shape and size of particle; at 1,625X and 4,500X a thin film of polymer could clearly be seen on the particles together with cluster structures which might have smaller coated particles of β-oestradiol, areas of excess polymerisation, or indeed both. The tendency to form clustered structures appeared at 832X and 2,250X more pronounced with the product from Example 2 with some agglomerate formation and some, presumably polymeric, trans-particle striation. The product from Example 3 gave a further increase in heterogeneous appearance but at 36,000X it was clear that the polymeric coating was not porous. Particles coated with the prepolymer (Example 4) were similar in appearance to those from Example 3.

The smaller particles of titanium dioxide did exhibit a polymeric coating but were substantially agglomerated.

EXAMPLE 7

This example describes in vitro studies on the release profiles of the encapsulated products of Examples 2, 3 and 4. Release was observed at 37°, 75°, 85°, and 100° C.

Release was effected as 37° C. by suspending a cellulose extraction thimble (ex Whatman: 10×50 mm) containing the encapsulated β-oestradiol into a conical flask containing 50 cm³ of buffer solution. The flasks were shaken at 37° C. in a constant temperature both (ex Grant Chemlab). Release was effected at the other temperatures by suspending the loaded thimble in a round bottomed flask containing 100 cm³ of buffer solution, equipped with a condenser, thermometer, temperature controlling unit (Fimonitor) and heated with a mantle heater.

Two stock solutions were utilised to prepare the phosphate buffer solution (pH 7.4) Solution A comprised 23.89 g of NaH₂PO₄.12H₂O (ex Fisons) dissolved in double distilled water qs to 1,000 cm³; Solution B comprises 9.07 g of KH₂PO₄ (ex Fisons) dissolved in double distilled water qs to 1,000 cm³. 10 cm³ of A and 4 cm³ of B diluted with double distilled water qs to 1,000 cm³ produced the required buffer solution.

A known weight of each encapsulated product was placed in a cellulose thimble which was sealed and then suspended in the flask of buffer solution. The solution and any released β-oestradiol were completely removed every 2 to 4 hours in the case of the 75°, 85° and 100° samples, every 1 to 7 days in the case of the 37° samples, and replaced by an equal volume of fresh buffer solution preheated to the same temperature. The recovered aliquots were then evaporated to dryness and the residue fractionally dissolved in chloroform (analytical reagent ex Fisons), filtered into a clean 25 cm³ volumetric flask, made up with chloroform to 25 cm³.

The quantity of β-oestradiol released at time t, $Q_t$, was estimated quantitatively from the UV absorbance at 280nm (Perkin Elmer 551 spectrophotometer). The results were plotted graphically and a continuous line was drawn through these points with smoothing to eliminate the background noise of the spectrophotometer that was used for the analysis.

The average delivery rate, at a given time was calculated by determining graphically the gradient at the corresponding point on the solid line.

BRIEF DESCRIPTION OF THE DRAWINGS

In the accompanying drawings, the figures represent graphically the average delivery rate, as ordinate, against time, as abscissa.

EXAMPLE 8

Figure 1:
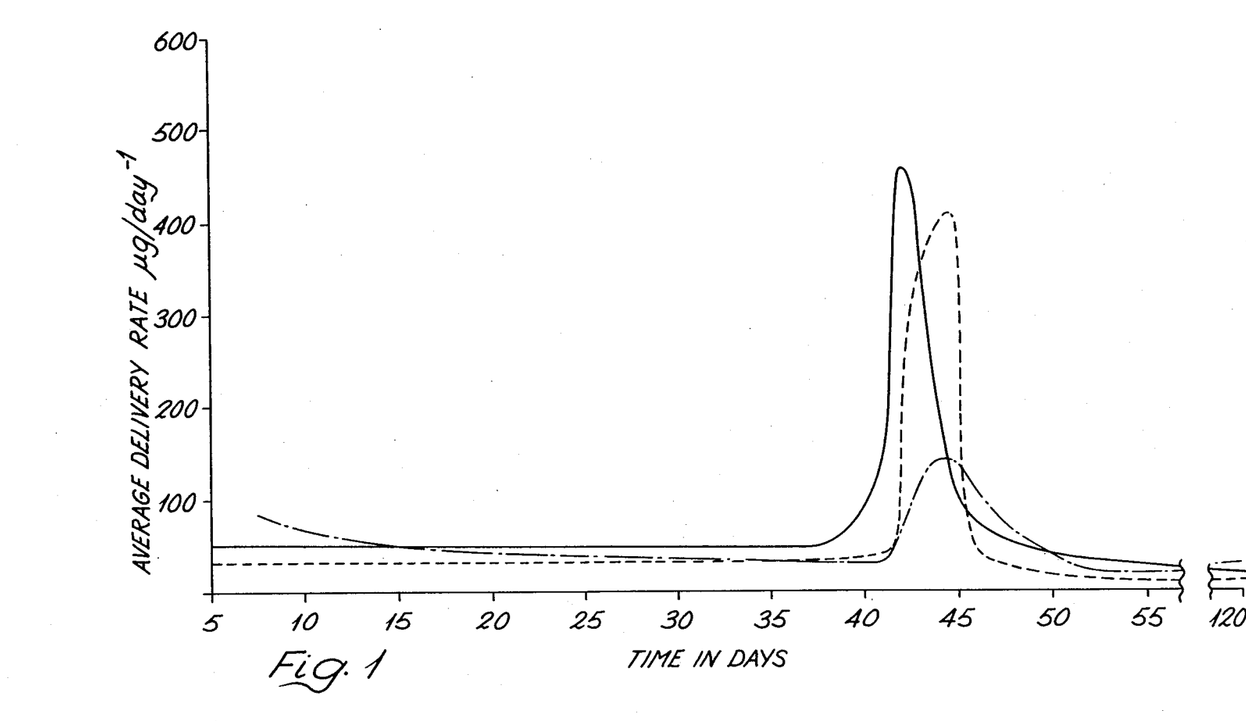
FIG. 1 represents the average delivery rate ($\mu$g day$^{-1}$) at 37° C. from the encapsulated product of Example 2, 3 and 4; shown respectively, as a solid, dotted, and chain dotted line against time (days)
Figure 2:
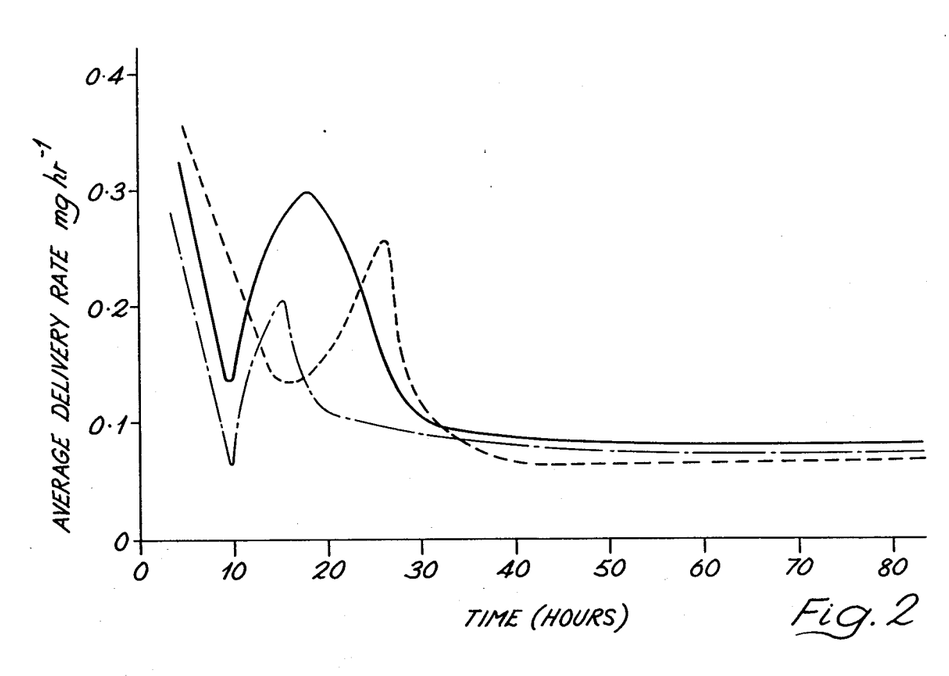
FIG. 2 represents the average delivery rate (mgh$^{-1}$) at 75° C. from the encapsulated product of Example 2, 3 and 4; shown, respectively, as a solid, dotted and chain line, against time (hours)
Figure 3:
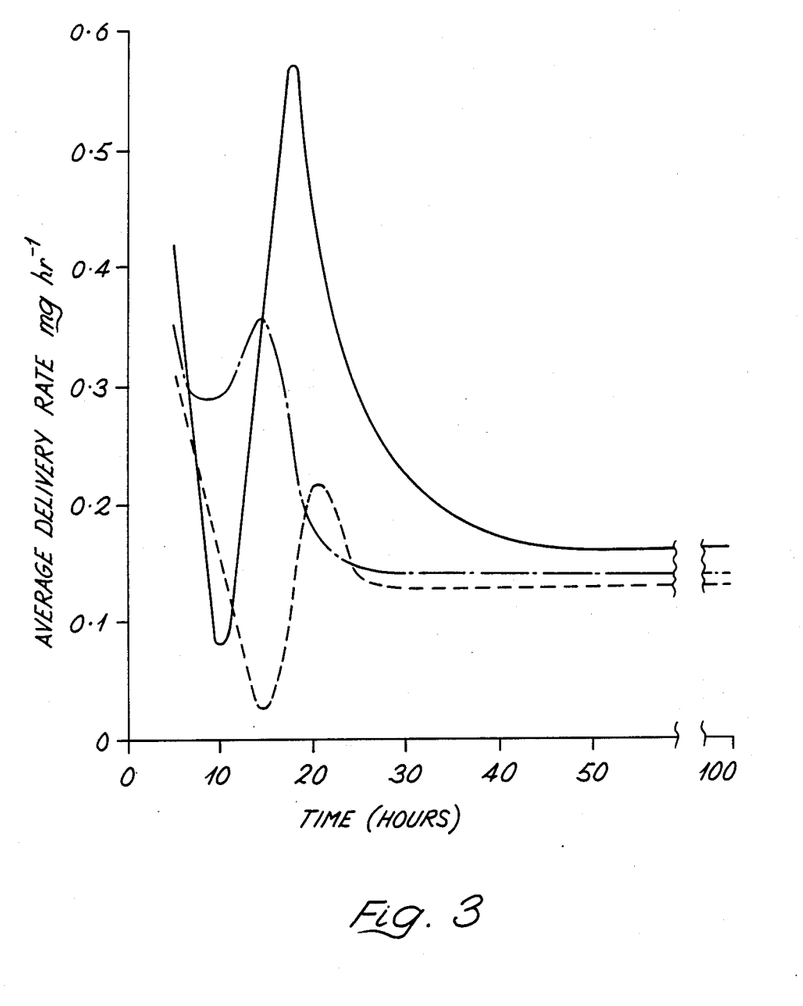
FIG. 3 represents the average delivery rate (mgh$^{-1}$) at 85° C. from the encapsulated product of Example 2, 3 and 4; shown, respectively, as a solid, dotted, and chain dotted line against time (hours)
Figure 4:
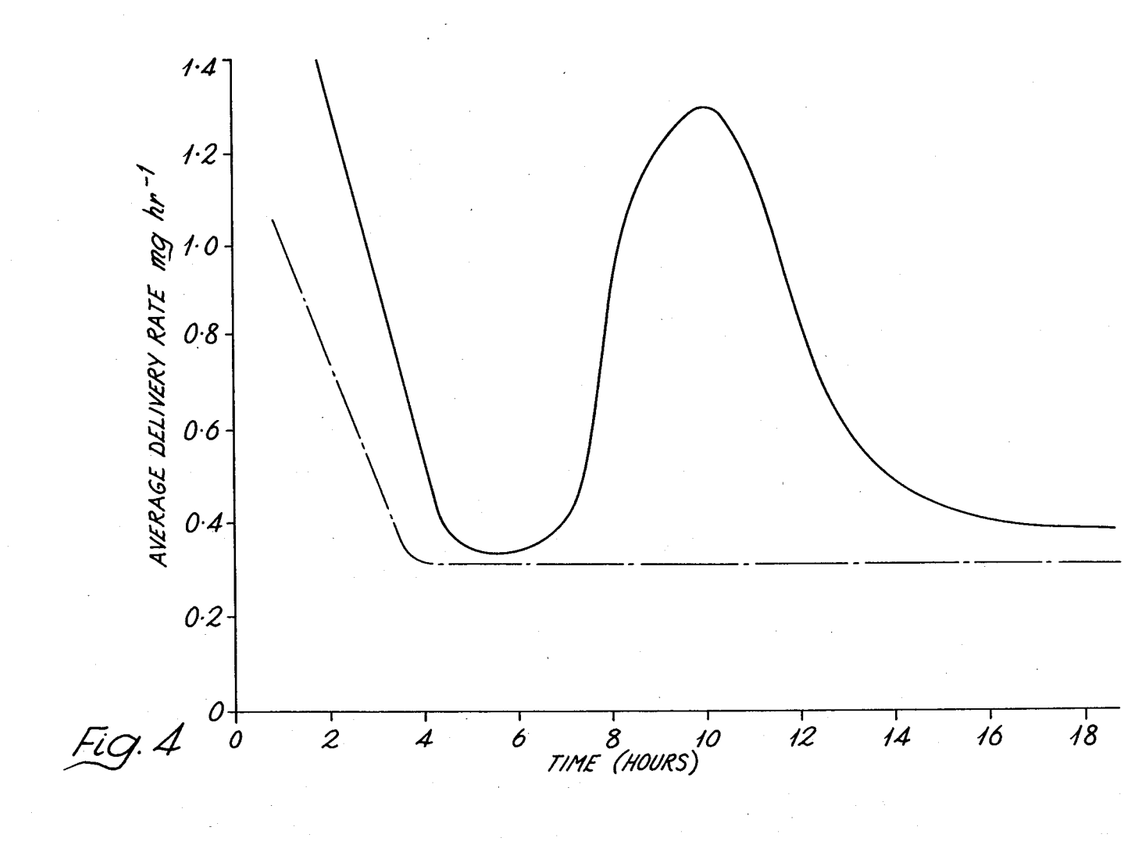
FIG. 4 represents the average delivery rate (mgh$^{-1}$) at 100° C. from the encapsulated product of Example 2 and 4 shown, respectively, as a solid and chain dotted line against time (hours)
Figure 5:
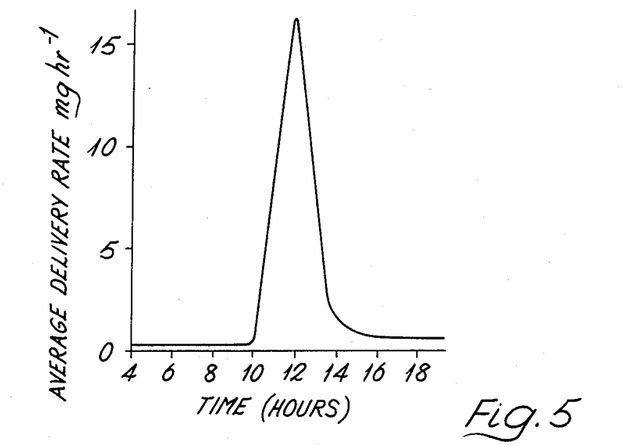
FIGS. 5 and 6 represent, upon the release data for the two independent experiments, the average delivery rate (mgh$^{-1}$) of encapsulated product of Example 3 against time (hours).
Figure 6:
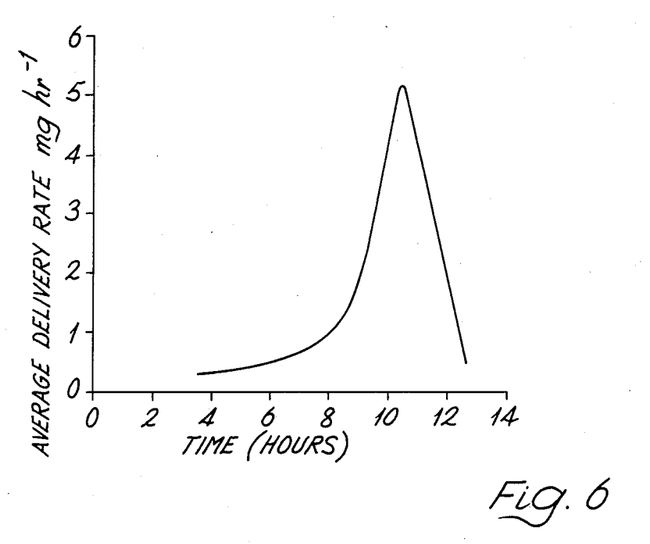

Example 1 was repeated using 0.2516 g pyrimethamine as active substance. 2 cm$^3$ of the α-monoolein solution; and 6 cm$^3$ of a 13.7% solution of acrolein tetramer in n-heptane.

EXAMPLE 9

Example 1 was repeated using 0.3600 g pyrimethamine; 2 cm$^3$ of the α-monoolein solution; and 6 cm$^3$ of a 20% solution of styrene in acetone. (Washing was effected with acetone instead of n-heptane.)

EXAMPLE 10

In vitro release studies on the release profiles of the encapsulated products of Examples 8 and 9 were made essentially as described in Example 7. Results are given in the following Table.

TABLE

| DAYS | PYRIMETHAMINE (%) | PYRIMETHAMINE AS IN EXAMPLE 8 (%) | PYRIMETHAMINE AS IN EXAMPLE 9 (%) |
|---|---|---|---|
| 1 | 27.64 | 15.096 | 17.42 |
| 4 | 56.12 | 42.25 | 42.42 |
| 5 | 75.59 | 58.99 | 51.37 |
| 6 | 86.01 | 68.66 | 58.25 |
| 7 | 91.07 | 72.66 | 63.11 |
| 8 | 94.32 | 81.46 | 69.01 |
| 11 | 97.63 | 84.81 | 71.19 |
| 12 | 98.72 | 86.29 | 73.26 |
| 13 | 99.55 | 87.22 | 75.44 |
| 14 | 100.01 | 87.96 | 77.62 |
| 15 | — | 88.31 | 79.86 |
| 18 | — | 88.69 | 82.04 |
| 19 | — | 88.78 | 84.22 |
| 20 | — | 88.87 | 87.06 |
| 22 | — | — | 87.67 |
| 25 | — | — | 89.02 |
| 26 | — | — | 90.02 |
| 27 | — | — | 91.31 |
| 28 | — | — | 92.57 |
| 33 | — | — | 94.87 |
| 34 | — | — | 95.99 |
| 35 | — | — | 96.96 |
| 36 | — | — | 97.76 |
| 37 | — | — | 98.56 |
| 38 | — | — | 99.07 |
| 39 | — | — | 99.13 |
| 40 | — | — | — |

In accordance with a further aspect of this invention, it may be desirable in order to reduce reaction time (especially with oral dosage forms) to incorporate in the encapsulating copolymer a hydrophilicity imparting comonomer or coprepolymer. The comonomer or coprepolymer may be derived from at least one of the following monomer classes.

(a) (meth)acrylic acid, (meth)acrylamide or an unsubstituted or hydroxy-substituted methyl or ethyl (meth)acrylate;

(b) a substituted or unsubstituted cyclic mono or poly ether having from 3 to 6 ring atoms; or (c) a substituted or unsubstituted vinyl alcohol, aldehyde, ether, acetal, ketone, ester or substituted or unsubstituted N-vinyl heterocyclic compound.

Desirably, the prepolymer comprises a homo- or copoly (alkylene oxide) such as poly(ethylene oxide).

We claim:

1. A composition which comprises at least one particle, the or each particle comprising an active substance-containing solid or liquid core encapsulated by a (co)polymer, which composition is obtained by treating at least one solid or liquid active substance-containing particle by adsorbing thereon at least one amphipathic compound and, if the amphipathic compound is not itself capable of acting as an initiator in cationic polymerization, activating the amphipathic compound with a Bronsted or Lewis acid so that it can function as an initiator in cationic polymerization; and encapsulating the at least one treated particle by the in situ (co)polymerization thereon, in a non-aqueous medium, of at least one cationically polymerizable monomer or prepolymer.

2. A composition according to claim 1 wherein the cationically polymerisable monomer or prepolymer comprises:

(a) a substituted or unsubstituted, cyclic or linear, mono- or poly-vinyl (thio)ether;

(b) a compound, other than as defined in (a), comprising at least one substituted or unsubstituted 3- or 4-membered ring comprising an oxa- or thia-hetero atom;

(c) a substituted or unsubstituted cyclic aliphatic anhydride;

(d) a substituted or unsubstituted aliphatic aldehyde; or (e) a substituted or unsubstituted mono- or poly-vinyl aromatic hydrocarbon; or (f) a substituted or unsubstituted mono- or poly-isocyanate.

3. A composition according to claim 2 wherein the cationically polymerisable monomer or prepolymer comprises an aromatic or aliphatic diepoxide.

4. A composition according to claim 2 or 3 wherein the cationically polymerisable monomer or prepolymer comprises a substituted or unsubstituted styrene or divinyl benzene.

5. A composition according to cliam 1 which is a controlled release composition.

6. A controlled released composition according to claim 1 wherein the encapsulated (co)polymer is hydrolysable.

7. A controlled release composition according to claim 6 wherein the (co)polymer comprises at least one non-pendant hydrolysable carboxylic ester, carbonate ester, amide, urethane, ketal or phosphate function.

8. A controlled release composition according to claim 1 wherein the cationically polymerisable monomer or prepolymer comprises a cyclic (thio)ether of the formula:

in which:
  $R_1$, $R_2$ and $R_4$, which may be the same or different, each represent a hydrogen atom or a substituted or unsubstituted hydrocarbyl or hydrocarbyloxy group;
  $R_3$ represents a substituted or unsubstituted methylene, ethylene or 1,3-propylene group;
  $R_5$ represents a monovalent polymerisable group;
  Q represents an oxygen or a sulphur atoms; and X represents:

in which:
  Y represents an oxygen atom or an —$NR_6$— group wherein $R_6$ represents any of the values which $R_1$ may assume;
  a is 0 or 1;
  b is 0 or 1;
  c is 1 or 2;
  d is 0 or 1;
with the proviso that at least one of b or d is 1, or a prepolymer thereof.

9. A controlled release composition according to claim 8 wherein X represents —COO— or —$CH_2OCO$—.

10. A controlled release composition according to claim 8 wherein the cationically polymerisable cyclic ether has the formula:

in which:
  $R_1$ $R_2$ and $R_4$, which may be the same or different, and $R_5$ are as defined in claim 8.

11. A controlled release composition according to claim 8 wherein the cationically polymerisable cyclic ether has the formula:

in which:
  $R_1$ $R_2$ and $R_4$, which may be the same or different, are as defined in claim 9; and
  $R_1'$, $R_2'$, and $R_4'$, which may the same or different, represent any of the values which $R_1$, $R_2$ and $R_4$ respectively may assume.

12. A controlled release composition according to claim 4 wherein the cationicaly polymerisable cyclic ether is acrolein tetramer.

13. A controlled release composition according to claim 8 wherein the cationically polymerisable monomer or prepolymer comprises a cyclic (thio)ether of the formula:

in which:
  $R_1$, $R_2$, $R_3$, $R_4$, $R_5$ and Q are as defined in claim 9; and
  X" represents:

in which:
  Y represents an oxygen atom or an —$NR_6$— group wherein $R_6$ represents any of the values which $R_1$ may assume;
  a is 0 or 1;
  b is 0 or 1;
  c is 0 or 1;
with the proviso that b+c is 1, or a prepolymer thereof.

14. A controlled release composition according to claim 8 wherein the cationically polymerisable monomer of prepolymer comprises a cyclic (thio)ether of the formula:

-continued in which:

R₁, R₂, R₃, R₄ and Q are as defined in claim 8;

R₁', R₂', R₃', R₁'', R₂'', R₃'', and R₄'' which may be the same or different, represent any of the values which R₁, R₂ and R₃ respectively may assume;

R₇ represents an n-valent hydrocarbon or poly(oxyhydrocarbon) residue of an n-hydroxy compound;

R₈ represents an n-valent non-hydrolysable bridging residue, or a prepolymer thereof.

15. The composition of claim 1, wherein the amphipathic compound is polyfunctional and is a cationically polymerizable monomer or prepolymer reactable with the at least one cationically polymerizable monomer or prepolymer.

16. A composition according to claim 15 wherein the amphipathic compound is a C₆ to C₃₆ saturated or unsaturated, aliphatic, cycloaliphatic, aromatic or araliphatic hydrocarbon which is substituted by a plurality of functional groups which comprise one or more hydroxyl groups, mercaptan groups, carboxylic acid groups and/or amide groups; and/or ester and/or amide groups which are themselves substituted by one or more of the said functional groups.

17. A composition according to claim 1 wherein the amphipathic compound is a monoester of a C₁₀ to C₂₀ monocarboxylic acid or a C₁₀ to C₂₀ monoalcohol with, correspondingly, a polyol or a polycarboxylic acid, or with a hydroxy acid.

18. A composition according to claim 1 wherein the amphipathic compound is a monoglyceride.

19. A composition according to claim 1 wherein the encapsulating polymer is chemically cross-linked.

20. A controlled release composition according to claim 1 wherein the active substance comprises a biologically active substance.

21. A controlled release composition according to claim 1 wherein the biologically active substance comprises a natural or synthetic steroid hormone.

22. A controlled release composition according to claim 1 wherein the steroid hormone comprises β-oestradiol.

23. A controlled release composition according to claim 1 wherein the biologically active substance is useful in the treatment of diabetes, pernicious anaemia or tropical disease.

24. A composition according to claim 1 dispersed in an inert liquid diluent.

25. An injectable composition according to claim 24 wherein the liquid diluent is sterile.

26. A controlled release composition according to claim 1 in an inert vapour.

27. An aerosol sprayable composition according to claim 26 wherein the vapour is under superatmospheric pressure.

28. A composition according to claim 1 for use in contraception.

29. A composition according to claim 1 wherein the active substance comprises a pigment.

30. The composition of claim 1, which comprises a plurality of particles comprising an active substance-containing solid or liquid core encapsulated by (co)polymer.

31. The controlled release composition according to claim 1, wherein the solid or liquid active substance-containing core particles have an average particle size not exceeding 1,000 microns.

32. A process for the preparation of a composition which comprises at least one particle comprising an active substance-containing solid or liquid core encapsulated by a (co)polymer, which process comprises treating at least one solid or liquid active substance-containing particle by adsorbing thereon at least one amphipathic compound and, if the amphipathic compound is not itself capable of acting as an initiator in cationic polymerization, activating the amphipathic compound with a Bronsted or Lewis acid so that it can function as an initiator in cationic polymerization; and encapsulating the at least one treated particle by in situ (co)polymerization thereon, in a non-aqueous medium, of at least one cationically polymerizable monomer or prepolymer.

33. A process according to claim 32, wherein the solid or liquid active-substance containing core particles have an average particle size not exceeding 1,000 microns.

34. A process according to claim 33 wherein the or each particle comprising at least one active substance is suspended in a liquid which is an inert non-solvent therefor.

35. A process according to claim 32 wherein the amphipathic compound is a C₆ to C₃₆ saturated or unsaturated, aliphatic, cycloaliphatic, aromatic or araliphatic hydrocarbon which is substituted by a plurality of functional groups which comprise one or more hydroxyl groups, mercaptan groups, carboxylic acid groups and/or amide groups; and/or ester and/or amide groups which are themselves substituted by one or more of the said functional groups.

36. A process according to claim 32 wherein the amphipathic compound is activated with boron trifluoride etherate.

37. A process according to claim 32 wherein the comonomer comprises a cyclic (thio)ether of the formula:

in which:

R₁, R₂ and R₄, which may be the same or different, each represent a hydrogen atom or a substituted or unsubstituted hydrocarbyl or hydrocarbyloxy group;

R₃ represents a substituted or unsubstituted methylene, ethylene or 1,3-propylene group;

R₅ represents a monovalent polymerizable group;

Q represents an oxygen or a sulphur atom; and x represents:

in which:
Y represents an oxygen atom or an —NR$_6$— group wherein R$_6$ represents any of the values which R$_1$ may assume;
a is 0 or 1;
b is 0 or 1;
c is 1 or 2;
d is 0 or 1; with the proviso that at least one of b or d is 1, or is a prepolymer thereof with at least one polyhydric alcohol.

38. A process according to claim 37 wherein the cationically polymerisable cyclic (thio)ether and the amphipathic compound are dissolved in solvents compatible with the inert non-solvent for the or each particles.

39. A process according to claim 32 wherein the encapsulation is repeated a plurality of times.

40. A process according to claim 32, wherein a plurality of active substance-containing core particles are liquid at ambient temperature, which process comprises first cooling them below their freezing point.

* * * * *